(12) United States Patent
Fenzl et al.

(10) Patent No.: US 9,895,453 B1
(45) Date of Patent: Feb. 20, 2018

(54) SHINY ULTRASOUND GEL

(71) Applicants: Mark Edward Fenzl, Bluffton, OH (US); Tonya Suzanne Fenzl, Bluffton, OH (US)

(72) Inventors: Mark Edward Fenzl, Bluffton, OH (US); Tonya Suzanne Fenzl, Bluffton, OH (US)

( * ) Notice: Subject to any disclaimer, the term of this patent is extended or adjusted under 35 U.S.C. 154(b) by 0 days.

(21) Appl. No.: 15/444,412

(22) Filed: Feb. 28, 2017

Related U.S. Application Data

(60) Provisional application No. 62/494,333, filed on Aug. 4, 2016.

(51) Int. Cl.
*A61K 49/22* (2006.01)

(52) U.S. Cl.
CPC .................. *A61K 49/226* (2013.01)

(58) Field of Classification Search
None
See application file for complete search history.

(56) References Cited

U.S. PATENT DOCUMENTS

| | | | |
|---|---|---|---|
| 8,273,024 B2 | 9/2012 | Chew et al. | |
| 8,618,175 B2 | 12/2013 | Heinar | |
| 2010/0112065 A1 | 5/2010 | Lauer | |
| 2010/0272769 A1* | 10/2010 | Darlington, Jr. | A01N 59/00 424/409 |
| 2012/0150033 A1 | 6/2012 | Rauch | |
| 2012/0237612 A1 | 9/2012 | Lampe | |
| 2015/0238410 A1 | 8/2015 | Klevtsov | |

FOREIGN PATENT DOCUMENTS

| | | |
|---|---|---|
| WO | 2005089344 A2 | 9/2005 |
| WO | 2014094127 A1 | 6/2014 |

OTHER PUBLICATIONS

Liu et al., "Nanoparticles as image enhancing agents for ultrasonography", Phys Med Biol 51: 2179-2189 (2006).*
Sutton Laboratories; Suttocide A: Preservative for Personal Care Products, 6. Retreived from: http://bbfactory.lv/media/SuttocideA.pdf, Chatham, New Jersey.
Mohammadsadeghi S., Abdorrasoul M., Zahedi S., & Eskandari F. (2013) The antimicrobial activity of elderberry (*Sambucus nigra* I.) extract against gram positive bacteria, gram negative bacteria and yeast. Research Journal of Applied Sciences 8 (4), 242. Iran.
Hammer K.A., Carson C.F., & Riley T.V. (1999) Antimicrobial activity of essential oils and other plant extracts. Journal of Applied Microbiology, 86, 986. Western Australia.

* cited by examiner

*Primary Examiner* — Robert A Wax
*Assistant Examiner* — Thor Nielsen
(74) *Attorney, Agent, or Firm* — Ward Law Office LLC; Jacob M. Ward

(57) ABSTRACT

An improved ultrasound gel adapted to have a shiny effect by adding glitter to an ultrasound gel, using a silver, reflective label and using a silver, reflective dispenser closure. This improved ultrasound gel is adapted to a pink *lavendula* lavender color by using the preservatives as coloring agents. Lavender essential oil is used as a perfume and preservative. The reflective glitter, reflective label, and reflective dispenser closure allow the ultrasonographer to better see the ultrasound gel and bottle in a darkened ultrasound room. The ultrasound gel is improved to have an aesthetic effect for the patient and healthcare provider by providing the combination of both a pink *lavendula* lavender color and a lavender scent.

14 Claims, No Drawings

SHINY ULTRASOUND GEL

CROSS-REFERENCE TO RELATED APPLICATIONS

This application claims the benefit of U.S. Provisional Patent Application Ser. No. 62/494,333, filed on Aug. 4, 2016. The entire disclosure of the above application is hereby incorporated herein by reference.

FIELD

The present invention relates to ultrasound gels and, more particularly, a glittery ultrasound gel with an improved appearance and scent.

BACKGROUND

Ultrasonography is the process of using an ultrasound machine that transmits ultrasound waves for a diagnostic or therapeutic purpose. Ultrasonography requires ultrasound gel to transmit ultrasound waves to and from the transducer on the ultrasound machine to the patient and back.

Throughout the process of ultrasonography, an ultrasonographer may place ultrasound gel on the patient multiple times using ultrasound gel from a bottle or container. Often an ultrasonographer will darken the room when performing ultrasonography in order to better visualize images on the ultrasound machine screen. In a dark room it may be difficult to see the ultrasound bottle and/or the ultrasound gel. Adding reflective glitter to the ultrasound gel and a reflective label and reflective closure increases the visibility of the ultrasound gel in a low light environment.

Many ultrasound gels contain FD&C coloring agents. Some people are allergic or have adverse reactions to FD&C coloring agents. Some people are also fearful of exposure to synthetic chemicals due to increased risk of cancer or other health conditions. There is also public fear of health risk associated with parabens and formaldehyde donor preservatives. Using natural products decreases exposure of the patient to synthetic chemicals.

There is a continuing need for an ultrasound gel that combines color and scent to create a pleasing aesthetic effect. Desirably, the ultrasound gel also has natural products as color additives, preservatives, and perfume.

SUMMARY

In concordance with the instant disclosure, an ultrasound gel that is reflective and combines color and scent to create a pleasing aesthetic effect, and which uses natural products as color additives, preservatives, and perfume, has surprisingly been discovered.

In an exemplary embodiment, an improved ultrasound gel is glittery, pink *lavendula* lavender colored, and lavender scented, and provided in a translucent bottle with a reflective, silver label and a reflective, silver dispenser closure. This ultrasound gel and bottle is easily seen in a darkened ultrasonography room due to the reflective nature of the glitter in the ultrasound gel and the reflective label and reflective closure on the ultrasound bottle. This unique ultrasound gel contains the preservatives Suttocide® A, elderberry extract, and lavender essential oil and does not contain parabens or formaldehyde donors or FD&C colors. This allows people that are fearful of the health risks or allergic reactions associated with paraben preservatives, formaldehyde donor preservatives, and FD&C colors to have the availability of ultrasound technology.

In a further embodiment, an improved ultrasound product container with a reflective label that allows the ultrasonographer to clearly see the ultrasound product container in a room with low ambient light.

In a further embodiment, an improved ultrasound product container with a reflective closure that allows the ultrasonographer to clearly see the ultrasound product container in a room with low ambient light.

The improved ultrasound gel is unique in that it combines color and scent to create a pleasing aesthetic effect. Flowers and fruit are attractive because they have both a pleasing color and scent. This unique ultrasound gel has a lavender scent and color. By using both a pleasing scent and color found in nature, the ultrasound gel creates an enjoyable experience for the patient and health care provider.

The improved ultrasound gel is shiny through the use of glitter, a silver metal or silver colored, reflective label on the bottle, and a silver metal or silver colored, reflective, disc top dispenser closure. The ultrasound gel does not contain parabens or formaldehyde donors and does not require an FD&C coloring agent because the preservative and natural products are used to color the ultrasound gel. The lavender scent creates an attractive aesthetic effect when combined with the pink *lavendula* lavender color of the ultrasound gel.

The ultrasound gel contains glitter that reflects light and allows the ultrasonographer to locate the ultrasound gel after it has been placed on the patient during the procedure in a room with low ambient light. Larger particles inhibit the conduction of ultrasound waves, therefore the glitter in this ultrasound gel has particles of 150 microns or smaller, or in other words less than 151 microns. The glitter also leaves a reflective glimmer on the skin of the patient after the procedure is over and the ultrasound gel is absorbed into the skin for a pleasant aesthetic effect.

The silver reflective label on the bottle provided a reflective surface that makes it easier for the ultrasonographer to see the bottle in low ambient light during ultrasonography. The reflective label also has a safety quality in that it allows the ultrasonographer to better read the label of the bottle to confirm that the ultrasonogapher is using the correct product in low ambient light.

The silver reflective disc top dispenser closure provides a reflective surface that makes it easier for the ultrasonographer to see the bottle. The dispenser closure also provides protection from antimicrobial contamination by preventing the user from touching the product or the product from returning to the container after the product has been dispensed.

Suttocide® A (Sodium Hydroxymethylglycinate) is a unique preservative that changes in a color range of pink to red color by combining it with citral. Combining the preservative Suttocide® A, with lemongrass essential oil, an essential oil which contains citral, surprisingly produces a unique ultrasound gel where the preservative and essential oil combination are used as a coloring agent. Elderberry extract, a natural product, is also a coloring agent. The glitter in the ultrasound gel is composed of mica and titanium dioxide. Suttocide® A, lemongrass essential oil, elderberry extract, mica, and titanium dioxide are not FD&C coloring agents.

Using the preservative and natural products as coloring agents provides a colorful ultrasound gel for persons that are allergic or have adverse reactions to FD&C coloring agents.

Aloe vera powder increases the absorption of water into skin and acts as an emollient. Adding aloe vera powder to the ultrasound gel allows the water of the formulation to be rapidly absorbed into the skin by rubbing it in at the end of the procedure. It also has a softening and soothing effect that lasts after the procedure.

Elderberry extract, and lavender essential oils have antimicrobial effects and can also be used as preservatives. Using sodium hydroxymethylglycinate, elderberry extract, and lavender essential oil as a preservative removes the need to use paraben or formaldehyde donor preservatives. Paraben and formaldehyde donor preservatives pose potential health risks that has created a concern for people that use topical products.

Lavender essential oil not only creates the lavender scent, but also provides an antimicrobial protection for the ultrasound gel. In this formulation the lavender essential oil not only provides an aesthetic effect by providing the lavender scent as part of the lavender flower scent and color. It also provides a preservative effect by its antimicrobial properties.

Chelating agents are agents that bind to metals. Adding a chelating agent or chelating agents to a natural ultrasound gel helps protect the ultrasound gel by inhibiting the growth of microbes by binding with materials they need for growth. This improved natural ultrasound gel uses sodium gluconate and citric acid as natural chelating agents. Using a natural chelating agent alleviates concerns for potential consumers about synthetic materials used in products that are in contact with their skin.

Essential oils can also have a palliative effect and a therapeutic effect, ant-stretch mark properties, and prevent the formation of stretch marks.

DETAILED DESCRIPTION

The following detailed description and appended drawings describe and illustrate various exemplary embodiments of the invention. The description and drawings serve to enable one skilled in the art to make and use the invention, and are not intended to limit the scope of the invention in any manner. In respect of the methods disclosed, the order of the steps presented is exemplary in nature, and thus, is not necessary or critical unless otherwise disclosed.

The term "ultrasound gel" refers to scanning gel or gels, transmission gel or gels, ultrasound gel or gels, ultrasound lotion or lotions, or any other solution designed or sold for the purpose of transmitting ultrasound waves.

The term "shiny" refers to a smooth surface that reflects light.

The term "luminescent" refers to the low temperature emission of light.

The term "glitter" refers to any particulate water insoluble coloring agent that creates a shimmer or glitters.

The term "neon color" refers to colors generated by noble gases or a combination of noble gases with or without mercury.

The term "fluorescent color" refers to a color that emits light after absorbing radiation.

The term "preservative" refers to a substance used to militate against decay.

The term "chelating agent" refers to a substance whose molecules can form bonds to a single metal ion.

The improved ultrasound gel of the present disclosure includes water, carbomer, propylene glycol, glycerol, sodium gluconate, citric acid, aloe vera powder, Suttocide® A (Sodium Hydroxymethylglycinate), elderberry extract, lavender essential oil, lemongrass essential oil, and glitter. The final product is a glittery gel, with a pink *lavendula* lavender color and a lavender scent in a translucent bottle with a silver, reflective label and a silver, reflective dispenser closure.

Ultrasound gels and cosmetics are regulated by the Food and Drug Administration (FDA). The reflective water insoluble powder color additive contains mica and titanium dioxide and particle size ranges from 30 to 150 microns. Mica and titanium dioxide are allowed as coloring agents according to the FDA. The FDA allows particulate coloring agents around the face and eyes in particle size equal or less than 150 microns. Elderberry extract is also used as a coloring agent. The FDA allows fruit juices as a coloring agent.

Suttocide® A (Sodium Hydroxymethylglycinate) kills *Escheria coli, Pseudomonas aeruginosa, Staphylococcus aureus, Aspergillus niger (Aspergillus brasiliensis)*, and *candida albicans* at a concentration of 0.7% as seen in TABLE 1. Suttocide® A is also a pH modifier that raises the pH of the product and can be used in concentrations of up to 1% for this benefit.

TABLE 1

Effect of Suttocide ® A on organism growth

| Organism | Initial Inoculum (per gram product) | 48 hours | 7 days | 28 days |
| --- | --- | --- | --- | --- |
| Staph aureus | $7.3 \times 10^6$ | <10 | <10 | <10 |
| E. Coli | $6.0 \times 10^6$ | <10 | <10 | <10 |
| Ps. aeruginosa | $9.5 \times 10^6$ | <10 | <10 | <10 |
| Ps. cepacia | $2.7 \times 10^6$ | <10 | <10 | <10 |
| C. ablicans | $4.3 \times 10^6$ | <10 | <10 | <10 |
| A. niger | $8.0 \times 10^6$ | <10 | <10 | <10 |

(Sutton Laboratories, page 6).

Elderberry Extract inhibits *Candida albicans, Escheria coli, Pseudomonas aeruginosa*, and *Staphylococcus aureus* at a concentration of 0.05%, as shown in TABLE 2.

TABLE 2

The Minimum Inhibitory Concentration (MIC) of *S. nigra* extract for gram positive and gram negative bacteria

| Bacteria/Yeast | MIC ($\mu g\ mL^{-1}$) |
| --- | --- |
| Staphylococcus aureus | 5 |
| Bacillus subtilis | 5 |
| Pseudomonas aerginosa | 3.32 |
| Escherichia coli | 2.7 |
| Salmonella typhi | 1.9 |
| Candida albicans | 0.625 |

(Mohammadsadeghi, Abdorrasoul, Zahedi, & Eskandari, 2013, page 242).

French Lavender essential oil inhibits *Candida albicans* and *Escheria coli* at concentrations of 0.5% as shown in TABLE 3.

TABLE 3

Minimum inhibitory concentrations (MICs) of selected essential oils (% v/v) against 10 different microorganisms

| Plant species | Lavandula argustifolia |
| --- | --- |
| Common name | French Lavender |
| Extract type | Essential Oil |
| Source | Flower |
| *Acinetobacter baumanii* | 1.0 |
| *Aeromonas sobria* | nd |

TABLE 3-continued

Minimum inhibitory concentrations (MICs) of selected essential oils (% v/v) against 10 different microorganisms

| Plant species | *Lavandula argustifolia* |
|---|---|
| Common name | French Lavender |
| Extract type | Essential Oil |
| Source | Flower |
| *Candida albicans* | 0.5 |
| *Enterococcus faecalis* | >2.0 |
| *Escherchia coli* | 0.5 |
| *Klebsiella pneumoniae* | 2.0 |
| *Pseudomonas aeruginosa* | >2.0 |
| *Salmonella typhimurium* | >2.0 |
| *Serratia marcens* | >2.0 |
| *Staphylococcus aureus* | 1.0 |

(Hammer, Carson, & Riley, 1999, page 986).

Together the preservatives, Suttocide® A, elderberry extract, and lavender essential oil protect the ultrasound gel from microbial contamination without using paraben or formaldehyde donor preservatives.

While certain representative embodiments and details have been shown for purposes of illustrating the invention, it will be apparent to those skilled in the art that various changes may be made without departing from the scope of the invention, which is further described in the following appended claims.

What is claimed is:

1. An ultrasound formulation, comprising:
   a carrier suitable for transmitting ultrasound waves;
   at least one preservative admixed with the carrier, wherein the preservative is not a paraben or formaldehyde donor;
   at least one essential oil with antimicrobial properties and admixed with the carrier; and
   reflective mica glitter having a particle size less than 151 microns, the glitter admixed with the carrier, wherein the glitter does not contain coal tar dyes.

2. The ultrasound formulation of claim 1, wherein the carrier includes a gel.

3. The ultrasound formulation of claim 1, wherein the preservative includes sodium hydroxymethylglycinate.

4. The ultrasound formulation of claim 1, wherein the essential oil includes lavender essential oil.

5. The ultrasound formulation of claim 1, further comprising elderberry extract.

6. The ultrasound formulation of claim 1, wherein the essential oil includes lemongrass essential oil.

7. The ultrasound formulation of claim 1, further comprising sodium gluconate.

8. The ultrasound formulation of claim 1, further comprising aloe vera powder.

9. The ultrasound formulation of claim 1, having a pink color.

10. The ultrasound formulation of claim 1, having a lavender scent.

11. An ultrasound product, comprising:
    an ultrasound formulation having
    a carrier suitable for transmitting ultrasound waves;
    at least one preservative admixed with the carrier, wherein the preservative is not a paraben or formaldehyde donor;
    at least one essential oil with antimicrobial properties and admixed with the carrier; and reflective mica glitter having a particle size less than 151 microns, the glitter admixed with the carrier, wherein the glitter does not contain coal tar dyes; and
    a container holding the ultrasound formulation, the container having a label with at least one of a glitter, a metallic reflective material, a neon color, a fluorescent color, and a light emitting material.

12. An ultrasound formulation with a container of claim 11, wherein the container has a reflective silver metal or silver colored label.

13. An ultrasound product, comprising:
    an ultrasound formulation having a carrier suitable for transmitting ultrasound waves;
    at least one preservative admixed with the carrier, wherein the preservative is not a paraben or formaldehyde donor;
    at least one essential oil with antimicrobial properties admixed with the carrier;
    reflective mica glitter having a particle size less than 151 microns, the glitter admixed with the carrier, wherein the glitter does not contain coal tar dyes; and
    a container holding the ultrasound formulation, the container having a closure including at least one of a glitter, a metallic reflective material, a neon color, a fluorescent color, and a light emitting material.

14. An ultrasound formulation with a container of claim 13, wherein the container has a reflective silver metal or silver colored disc closure.

* * * * *